(12) United States Patent
Fogal et al.

(10) Patent No.: US 8,592,178 B2
(45) Date of Patent: Nov. 26, 2013

(54) PROCESS FOR THE PREPARATION OF TESTOSTERONE

(75) Inventors: Stefano Fogal, Altivole (IT); Elisabetta Bergantino, Cadoneghe (IT); Riccardo Motterle, Arcugnano (IT); Andrea Castellin, Mestrino (IT); Giancarlo Arvotti, Montecchio Maggiore (IT)

(73) Assignee: F.I.S. Fabbrica Italiana Sintetici S.p.A., Alte di Montecchio Maggiore (IT)

( * ) Notice: Subject to any disclaimer, the term of this patent is extended or adjusted under 35 U.S.C. 154(b) by 208 days.

(21) Appl. No.: 13/119,915

(22) PCT Filed: Jun. 15, 2010

(86) PCT No.: PCT/EP2010/058411
§ 371 (c)(1),
(2), (4) Date: Apr. 12, 2011

(87) PCT Pub. No.: WO2011/000693
PCT Pub. Date: Jan. 6, 2011

(65) Prior Publication Data
US 2011/0207172 A1 Aug. 25, 2011

(30) Foreign Application Priority Data
Jul. 1, 2009 (IT) .............................. MI2009A1168

(51) Int. Cl.
*C12P 33/16* (2006.01)
*C12N 9/00* (2006.01)
*C12N 9/04* (2006.01)
*C12N 1/20* (2006.01)
*C12N 15/00* (2006.01)
*C07H 21/04* (2006.01)

(52) U.S. Cl.
USPC .......... 435/55; 435/183; 435/190; 435/252.3; 435/320.1; 536/23.2

(58) Field of Classification Search
None
See application file for complete search history.

(56) References Cited

U.S. PATENT DOCUMENTS 5,643,758 A * 7/1997 Guan et al. ................... 435/69.7

FOREIGN PATENT DOCUMENTS

WO WO 00/56879 A1 9/2000
WO WO 2007/118644 A1 10/2007

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession P70694, Jul. 15, 1999.*
Dufort et al. Endocrinology. Feb. 1999;140(2):568-74.*
Dufort et al., "Characteristics of a Highly Labile Human Type 5 17-beta-hydroxysteroid Dehydrogenase" Endocrinology, vol. 140, pp. 568-574, 1999.
Cèbe et al., "Rapid and Easy Thermodynamic Optimization of the 5' -end of mRNA Dramatically Increases the Level of Wild Type Protein Expression in *Escherichia coli*." Protein Expression and Purification, vol. 45, pp. 374-380, 2006.
Lu et al., "Purification, Reconstitution and Steady-State Kinetics of the Trans-Membrane 17-beta-hydroxysteroid, Dehydrogenase 2." The Journal of Biological Chemistry, vol. 277, pp. 22123-22130, 2002.
Brinkmann et al., "Inhibition of Tryptase TL2 from Human T4+ Lymphocytes and Inhibition of HIV-1 Replication in H9 Cells by Recombinant Aprotinin and Bikunin Homologues." Journal of Protein Chemistry, vol. 16, pp. 651-660, 1997.
Churchill et al., "Rapid Purification of Recombinant Listeriolysin 0 (LLO) from *Escherichia coli*." Journal of Industrial Microbiology and Biotechnology, vol. 32, pp. 355-363, 2005.
Stefano et al., "Biocatalyzed Synthesis of Testosterone." Chemical Engineering Transactions, vol. 20, pp. 61-66, Apr. 2010.
P. Rheault et al., "Structure and Activity of the Murine Type 5 17β-hydroxysteroid Dehydrogenase Gene,"Biochimica et Biophysica Acta, vol. 1447, No. 1, pp. 17-24 (1999).

* cited by examiner

*Primary Examiner* — Christian Fronda
(74) *Attorney, Agent, or Firm* — Dickstein Shapiro LLP

(57) ABSTRACT

The present invention relates to an industrial process for the reduction of 4-androstene-3,17-dione in order to obtain testosterone using a particularly stable and selective enzyme produced in a recombinant manner.

13 Claims, 8 Drawing Sheets

FIG. 2

Ndei
GCTGAGAACATATGGATTCTAAG (forward)
5'GTATCTTCTCAGTTGGTGGGCTGAGAAGCCATGGATGATTCTAAGCAGCAGAGACAGTGCGTCTAAGTGATGGTCACTTCATCCCTATACTGGGTTTGGTA
CCTATGCCACCTCAAGAGGTACCTAAGAGATGAAGGCTACAGAGAGCTACTAAAATAGCCATAGATGCTGGTTTCCGCCATATTGATTCGCTTCTATGTATCA
AAATGAAAAGGAAGTAGGACTAGCCATCCGAAGCAAGATAGCCACTGTGAAGAGGAAGATATATTTACACATCAAAGGTTTGGTGTACTTT
TCATCGTCCAGAACTCGTACGGGTCTGCTTGGAACAGTCATTGAACAACTCCAGTTGGACTATGTGGATTATCTGTGGATATCTGTGACACCTGGGAAGCCAT
GAAGCCGGGAGAAAATTATCTCCAAAAGATGAAAATTAATATATGATGCTGTGGATATCTGTGACACCTGGGAAGCCATGGGAGAAATGCAA
GGATGCCAGGATTGGCCAAGTCCATTGGGGTGTCCAAACTTTAACCGCAGGCAGCTGGAGAAGATCCTGAAAAAGCCGGGGCTCAAGTACAAGCCTGTGTG
CAACCAGTAGAATGTCATCCTTATCTCAGGGAAAACTTCTGATTTCTGCAGTCAAAAGACATTGTTCTGGTTGCTTACAGTGCTCTCTGGGAAG
CCATCGTGAAAAACAATGGGTTGATCAGAGCTCCTCGTCTTTTGGATAATCAGTTCTTGGCTCAATGGAGTACAATCGAACTCCGCGCT
GATTGCCCTTCGGCTACCAGGACTACAACCGTGGGGTTGTGGTCCTGATGAATAAAGATATCGATACATAAGTGGTTCTAGCTTTAAGGACCATCCTGATTTTCA
GTTGACTTCAGAGGACATGAAAGTCCTCGATGACCTGAATAAAGATATCGATACATAAGTGGTTCTAGCTTTAAGGACCATCCTGATTTTG
GGATGAATACTAACTGGAGGTCCATTTTGTGCCTTGTGCCAGATGTCACTGCATTGGAAGAGTGTATAGAAGAAGCCAAAATGTGATGATTACA
TATCACCCTAATCGAATTCTGGCCAATTCTGGCCAATTCTGAGCAATTCTGAGCAATTCGGAGCTCTAGGAAAAATCTGGTTGAAACAAGAAAAGCCAAAACTATGTATATTTCTCCTTTCAAGAAA
TAAAAGAATCGTTATTCTTTAGCATTTAAAAAAAAAAAAGGCGGCCGCTCAGAGTATCCCTGAGGGGCCCAAGCTT NotI

FIG. 3A

17β-HSD5 murine (SEQ. ID n 1)

MDSKQQTVRLSDGHFIPILGFGTYAPQEVPKSKATEATKIAIDAGFRHIDSASMYQNEKEVGLAIRSKIADGTV
KREDIFYTSKVWCTFHRPELVRVCLEQSLKQLQLDYVDLYLIHFPMAMKPGENYLPKDENGKLIYDAVDICDT
WEAMEKCKDAGLAKSIGVSNFNRRQLEKILKKPGLKYKPVCNQVECHPYLNQGKLLDFCRSKDIVLVAYSAL
GSHREKQWVDQSSPVLLDNPVLGSMAKKYNRTPALIALRYQLQRGVVVLAKSFSEKRIKENMQVFEFQLTS
EDMKVLDDLNKNIRYISGSSFKDHPDFPFWDEY

FIG. 3B

17β-HSD5 recombinant murine (SEQ. ID n 2)

MGSSHHHHHHSSGLVPRGSHMDSKQQTVRLSDGHFIPILGFGTYAPQEVPKSKATEATKIAIDAGFRHIDSA
SMYQNEKEVGLAIRSKIADGTVKREDIFYTSKVWCTFHRPELVRVCLEQSLKQLQLDYVDLYLIHFPMAMKPG
ENYLPKDENGKLIYDAVDICDTWEAMEKCKDAGLAKSIGVSNFNRRQLEKILKKPGLKYKPVCNQVECHPYL
NQGKLLDFCRSKDIVLVAYSALGSHREKQWVDQSSPVLLDNPVLGSMAKKYNRTPALIALRYQLQRGVVVLA
KSFSEKRIKENMQVFEFQLTSEDMKVLDDLNKNIRYISGSSFKDHPDFPFWDEY

FIG. 8
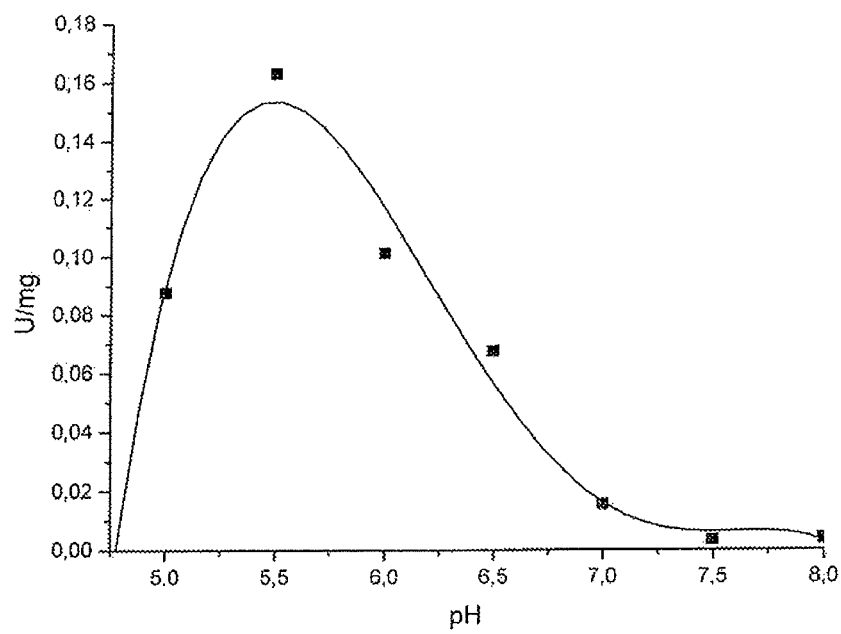
Activity profile per milligram with NADPH
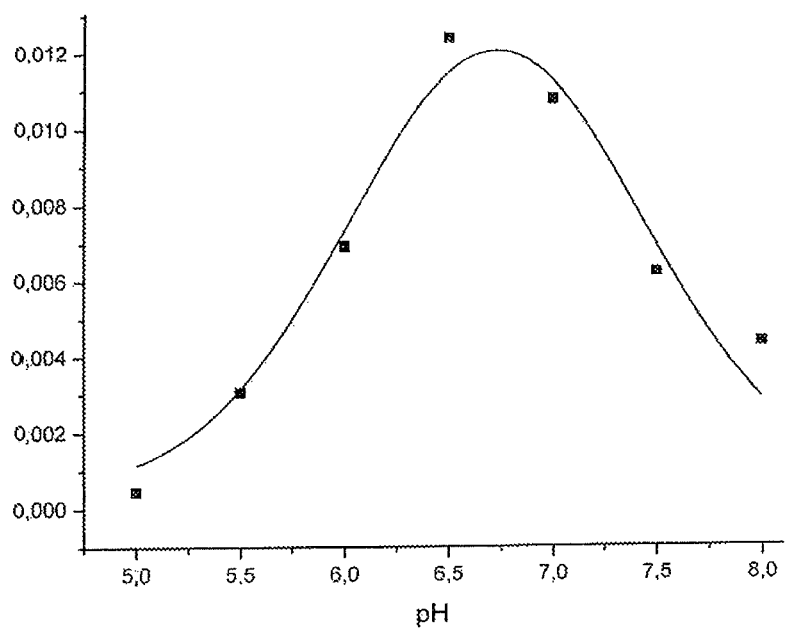
Activity profile per milligram with NADH

PROCESS FOR THE PREPARATION OF TESTOSTERONE

The object of the present invention is a process for the industrial preparation of testosterone from 4-androstene-3, 17-dione through the chemo- and stereo-selective enzymatic reduction of the carbonyl group at C17.

In nature, the synthesis in vivo of testosterone comprises the reduction of the 4-androstene-3,17-dione carbonyl group at C17 by enzymes known as the 17β-hydroxysteroid dehydrogenases (17β-HSD).

The use of human type V 17β-hydroxysteroid dehydrogenases (17β-HSD5) for the synthesis of testosterone in vitro has already been described. Dufort et al (Endocrynology, 1999, Vol. 140, No. 2; p 568-574) in 1999 have used human 17β-hydroxysteroid dehydrogenase expressed in cultured human cells and have studied their capacity of converting the 4-androstene-3,17-dione into testosterone and the dihydrotestosterone in 3α-17β-androstanediol. However, there resulted a low enzyme regioselectivity, which has resulted to be poorly stable, as indicated by the rapid activity decrease during the purification step, both when it is recombinantly expressed in human and bacterial cells such as Escherichia coli.

The same murine type V 17β-hydroxysteroid dehydrogenase enzyme has proven to be more stable and more regioselective than the human homologue (75% sequence identity), as described in the work by Dufort et al (Endocrynology, 1999, Vol. 140, No. 2; p 568-574).

In the same article, it is also reported that the conversion from 4-androstene-3,17-dione to testosterone using a human type V 17β-hydroxysteroid dehydrogenase is as low as 25%, whereas the same reaction carried out by means of a murine type V 17β-hydroxysteroid dehydrogenase provides a conversion around 60%. No other data concerning the purity of the product and the selectivity of the reduction reaction is provided therein.

In the application PCT WO2007/118644 by IEP GmbH, the Example 1 reports that the in vitro conversion from 4-androstene-3,17-dione into testosterone using a 17β-hydroxysteroid dehydrogenase from Pseudomonas testosteroni ranges within 90-95%. In U.S. Pat. No. 2,796,382 filed on Oct. 9, 1953 by Paul Talalay, the conversion of 4-androsten-3,17-dione into testosterone, still using a 17β-hydroxysteroid dehydrogenase from Pseudomonas testosteroni, is said to be quantitative but it is calculated on the base of the cofactor consumption and in fact no purity data of the resulting product is ever reported. Moreover, it is well known that the biocatalytic processes suffer from low reproducibility and low stability of the enzymes, therefore making said processes non convenient for industrial scale applications.

The object of the present invention is, accordingly, an industrial process for preparing testosterone from the reduction of 4-androstene-3,17-dione using a more stable enzyme, suitably prepared and purified, which allows obtaining greater reproducibility of the results and higher chemoselectivity and conversion rate.

BRIEF DESCRIPTION OF THE DRAWINGS

FIG. 2 is the nucleotide sequence of the murine type V 17β-hydroxysteroid dehydrogenase enzyme, wherein the mutagenic primer forward is underlined and the start and end codons, and the restriction sites used are written in bold. FIG. 3A is the amino acid sequence of the murine type V 17β-hydroxysteroid dehydrogenase enzyme, whereas FIG. 3B is the amino acid sequence of the murine type V 17β-hydroxysteroid dehydrogenase enzyme modified according to the present invention;

FIG. 8 shows the activity of the enzyme as a function of the pH in water at room temperature employing two different cofactors.

DETAILED DESCRIPTION OF THE INVENTION

Figure 1:
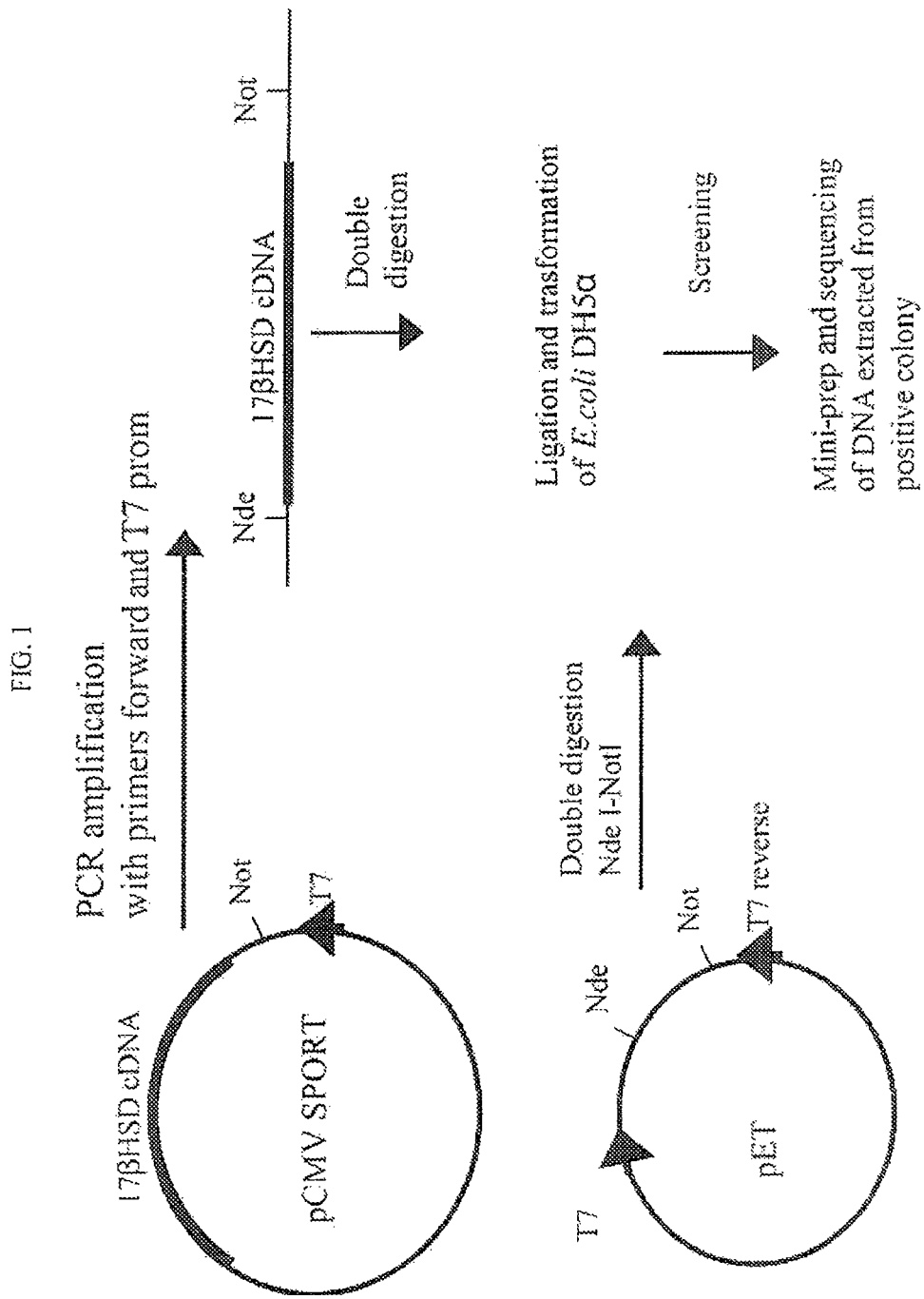
FIG. 1 is an illustration of the cloning diagram of the gene codifying for the murine type V 17β-hydroxysteroid dehydrogenase according to the present invention.

The object of the present invention is an industrial process for preparing testosterone from the reduction of 4-androstene-3,17-dione using the recombinant murine type V 17β-hydroxysteroid dehydrogenase enzyme (17β-HSD5).

According to a preferred embodiment of the invention, the used recombinant murine type V 17β-hydroxysteroid dehydrogenase enzyme has a sequence corresponding to the SEQ ID n. 2.

According to a more preferred embodiment, said enzyme has been purified.

Particularly, said process is carried out according to the following scheme

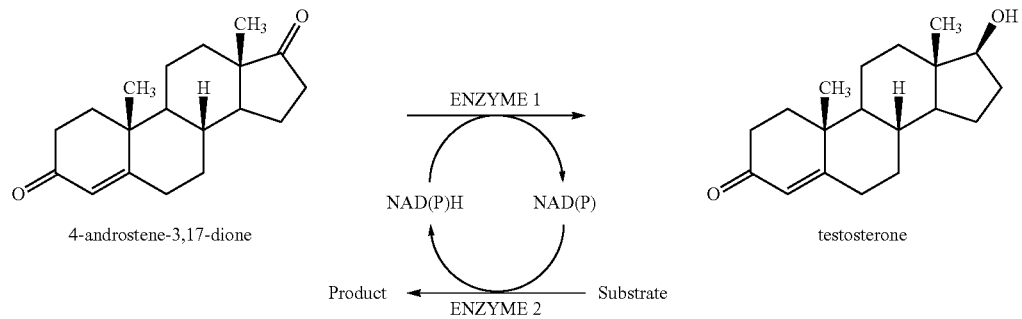

wherein the enzyme 1 is the recombinant murine type V 17β-hydroxysteroid dehydrogenase, which catalyzes the chemo- and regioselective reduction of the 4-androstene-3,17-dione carbonyl group at C17, NAD(P)H is the reduced nicotinamide-adenine-dinucleotide (phosphate) acting as a cofactor. The enzyme 2 is a dehydrogenase used for recycling the cofactor to the detriment of a substrate that is oxidized.

Advantageously, the process of the present invention allows retrieving and recycling the cofactor using dehydrogenases that regenerate the NADPH or the less expensive NADH due to the addition of a suitable substrate.

More particularly, in order to carry out the process of the present invention a buffering solution, a solvent, the cofactor, the cofactor-regenerating dehydrogenase enzyme and a suitable substrate are loaded to a magnetically stirred thermostated vial. The mixture is then stirred from 20° C. to 35° C. and 4-androstene-3,17-dione along with the recombinant murine type V 17β-hydroxysteroid dehydrogenase enzyme of the present invention are added thereto. The reaction mixture is then vigorously stirred at room temperature for a sufficient period of time. When the reaction has been accomplished, the testosterone is extracted by means of a suitable solvent, the phases are filtered, separated and the organic phase is concentrated to dryness. The process yield is surprisingly almost quantitative and the purity of the obtained testosterone even more surprisingly ranges between 98% and 100% (HPLC A %).

In more detail, the mixture pH must be kept within the range of 4.0 to 9.0. To the purpose, a suitable buffer, for example, can be used.

The buffer can be used either alone or with solvents and co-solvents, such as, for example, methanol, ethanol, isopropanol, tert-butanol, glycerol, dimethyl sulfoxide (DMSO), acetonitrile or dimethylformamide (DMF).

As described above, advantageously, the process of the invention allows regenerating the cofactor by means of a suitable dehydrogenase. A glucose dehydrogenase can be used, and accordingly, glucose as the substrate will be added to the reaction, thereby obtaining gluconic acid along with the regenerated cofactor. Alternatively, the formate dehydrogenase enzyme can be used by adding the sodium formate substrate. Alternatively, other known systems can be used for the enzymatic or chemical regeneration of the cofactor.

In turn, when used in catalytic amounts, the cofactor can be either NAD(H) or NADP(H), NAD(H) being however preferred as it is less expensive.

As relates to the enzyme used in the process of the present invention, this is the murine type V 17β-hydroxysteroid dehydrogenases (17β-HSD5), suitably modified such as to enable the purification thereof. The enzyme amino acid sequence is shown in FIG. 3B.

Particularly, for the purposes of the present invention, the murine type V 17β-hydroxysteroid dehydrogenase enzyme has been modified by the addition of the tail MGSSHHHH-HHSSGLVPRGSH at the N-terminal end comprising a peptide segment consisting of consecutive histidines (His-Tag) so that the sequence thereof results to be (See SEQ ID n. 2):

MGSSHHHHHHSSGLVPRGSHMDSKQQTVRLSDGHFIPILGFGTYAPQEVP

KSKATEATKIAIDAGFRHIDSASMYQNEKEVGLAIRSKIADGTVKREDIF

YTSKVWCTFHRPELVRVCLEQSLKQLQLDYVDLYLIHFPMAMKPGENYLP

KDENGKLIYDAVDICDTWEAMEKCKDAGLAKSIGVSNFNRRQLEKILKKP

-continued
GLKYKPVCNQVECHPYLNQGKLLDFCRSKDIVLVAYSALGSHREKQWVDQ

SSPVLLDNPVLGSMAKKYNRTPALIALRYQLQRGVVVLAKSFSEKRIKEN

MQVFEFQLTSEDMKVLDDLNKNIRYISGSSFKDHPDFPFWDEY

The enzyme has been cloned and expressed in *Escherichia coli* according to the procedures described in the following experimental section. The person skilled in the art will recognize that other cloning vectors might be suitably used such as *S. cerevisiae* or *P. pastoris*.

The thus-prepared enzyme can be quickly purified as described in the experimental section. The following advantages are achieved: 1. Protection from the proteolytic degradation during the purification step; 2. Protection from the proteolytic degradation during the reaction step; 3. Substantial reduction in the potential side-reactions due to enzymes that are present in the cell paste or co-purified. The transformation of the 4-androstene-3,17-dione into testosterone is thus carried out surprisingly with high chemo- and regioselectivity and reproducibility of results, with an almost quantitative conversion and unexpectedly not generating further by-products.

Materials and Methods

The following solutions have been prepared, in which SB designates the solubilization buffer.

Kanamycin (50 mg/mL) are dissolved in 50 mL milliQ water. The solution is filtered in sterile environment using a 0.22 µm filter. Storage at −20° C.

Solution A (LB Agar Kanamycin 50 µg/mL for Plates

For 1 liter of solution the following amounts were poured in a becker:

| Tryptone | 10 g |
|---|---|
| Yeast extract | 5 g |
| NaCl | 5 g |

It was dissolved in deionized water and brought to 1 L final volume. The pH was brought to 7.5 by adding 1M NaOH solution (about 1 mL). The solution was transferred into 1 L autoclavable bottles and 15 g agar (for bacterial cultures) was added. This was autoclaved at 120° C. for 20 minutes at 2 bar. In a sterile environment, the bottled solution was left to cool to about 50-60° C. (before solidification). 1 mL Kanamycin solution (50 mg/mL) was added. The bottle was stirred. About 20 mL solution per plate was added before the medium had solidified and the plates were left uncovered to complete solidification. The plates were closed and stored in a sterile environment at 4° C. (for max 1-2 months).

Solution B (LB agar Kanamycin 50 microg/mL for Culture in 1 L Flasks)

The following amounts were poured into a becker:

| Trypton | 10 g |
|---|---|
| Yeast extract | 5 g |
| NaCl | 5 g |

This was dissolved in deionized water and brought to 1 L final volume. The pH was brought to 7.5 by adding 1M NaOH solution (about 1 mL). The solution was transferred into autoclavable flasks according to the requirements, with gauze and cotton plugs. This was autoclaved at 120° C. for 20 minutes and left to cool to room temperature in a sterile environment. 1 mL Kanamycin solution (50 mg/mL) (see above) was added.

Solution C (IPTG 5 mL 0.5 M Solution)

0.595 g Isopropil β-D-1-thiogalactopyranoside was weighed and dissolved in 5 mL milliQ water. The solution as filtered in a sterile environment by means of a 0.22 μm filter. This was stored at −20° C.

Solution D (SB=Solubilization Buffer 1X 30 mL)

10 mL SB3X solution was diluted with 20 mL deionized water.

This was stored at −20° C. and resuspended after thawing.

Solution E (SB3X 40 mL)

16 mL TRIS 0.125 mM pH 6.8 was added to 12 g glycerol. 3.6 g SDS and 0.62 g DTT was added thereto. Several tens of milligrams of bromophenol blue were mixed and added thereto. This was brought to volume with deionized water, stored at −20° C., and resuspended after thawing.

Solution F (5 mM Imidazole Buffer for Balancing 2 Liter Column)

In 1.5 l mQ water the following was dissolved:

| | |
|---|---|
| NaCl | 43.8 g |
| Sodium phosphate (NaH$_2$PO$_3$) | 1.8 g |
| Na$_2$HPO$_3$•12H$_2$O | 5.4 g |
| Imidazole | 0.57 g |

This was brought to volume and brought to pH 7.4 by means of HCl 1 M or NaOH 1 M. Filtration was carried out by means of 0.22 μm filter.

Solution G (Buffer 500 mM Imidazole for Elution)

In 1.5 l mQ water the following was dissolved:

| | |
|---|---|
| NaCl | 43.8 g |
| Sodium phosphate (NaH$_2$PO$_3$) | 1.8 g |
| Na$_2$HPO$_3$•12H$_2$O | 5.4 g |
| Imidazole | 51.6 g |

This was brought to volume, and to pH 7.4 by means of HCl 1 M or NaOH 1 M. Filtering was carried out by means of 0.22 μm filter.

Cloning

All the cloning procedures below described have been carried out according to the instructions stated in Sambrook and Russel; Molecular Cloning—a Laboratory Manual (3$^{rd}$ Edition), CSHL Press (2001—New York). For the cloning, the pET28a plasmid (Novagen, Darmstadt-Germany) has been used for the *E. coli* (strain BL21) expression, so as to allow the expression of the fusion protein to a tag of six amino-terminal histidines. The cDNA codifying for the murine type V 17β-hydroxysteroid dehydrogenase enzyme has been obtained from the ImaGenes GmbH library (Berlin, Germany), contained in the pCMV SPORT 6 plasmid vector (FIG. 1). The nucleotide sequence has been controlled by means of sequencing and based thereon the primer 5'-GCT-GAGAACATATGGATTCTAAG-3', has been designed, which contains the restriction site NdeI (containing the ATG start codon for the translation). This primer (forward), together with the T7 promoter 5'-TAATACGACTCAC-TACA-3' primer (reverse), has been used in a PCR reaction (polymerase chain reaction) for the amplification of the cDNA of interest.

The product obtained has been digested by digestion by the NdeI and NotI enzymes, the latter provided in the pCMV SPORT 6 plasmid, downstream of cDNA (see FIG. 1). The same double digestion has been carried out on the pET28a plasmid. Both digestion products have been gathered by means of T4-DNA ligase and the ligation product used for the transformation of *E. coli* DH5α cells by means of electroporation.

The transformed cells have been plated in LB agar with 50 μg/mL kanamycin and incubated overnight at 37° C. Of the grown colonies, 19 have been subjected to screening by means of PCR for identifying the clones containing the recombinant plasmid of interest (pET28a containing the cDNA the murine type V 17β-hydroxysteroid dehydrogenase enzyme, hereinafter called p17βHSD), using the primer T7 promoter and T7 terminator (FIG. 1). A colony positive to screening has been used for inoculating 5 mL LB with 50 μg/mL kanamycin and the bacterial culture has been left to grow overnight at 37° C. The bacterial culture has been subsequently used for extracting the p17βHSD plasmid by means of mini-prep (Quiagen). The purified plasmid has been sequenced using the T7 promoter primer and T7 terminator, in order to control the correct sequence thereof.

Small-Scale Expression and Purification of the Recombinant Murine Type V 17β-Hydroxysteroid Dehydrogenase Enzyme The expression plasmid p17βHSD has been introduced in *E. coli* cells of the BL21 strain by means of chemical transformation (CaCl$_2$). The cells have been subsequently plated in LB agar with 50 μg/mL kanamycin and incubated overnight at 37° C. under stirring. Several colonies have been used for inoculating a pre-culture of 5 mL LB 50 μg/mL kanamycin, grown overnight at 37° C., which has been used as inoculum for 2.5 L culture in a flask. The culture has been amplified at 37° C. under stirring at 200 rpm, until reaching an optical density at 600 nm (OD$_{600}$) of 0.85, then IPTG (Isopropyl β-D-1-thiogalactopyranoside, protein expression inducer) has been added thereto at a final concentration of 0.1 mM.

After 18 h growth the culture broth has been collected and centrifuged at 6000 G for 10 minutes at 4° C. After the supernatant has been eliminated, the bacterial pellet has been resuspended in 800 mL phosphate buffer 100 mM pH 7.2 and centrifuged again at 6000 G for 10 minutes at 4° C.

The washed bacterial pellet has been resuspended in 70 mL of solution F (20 mM Na phosphate buffer pH 7.4, 500 mM NaCl, 5 mM Imidazole). The bacteria have been then lysated by means of sonication and the solution has been centrifuged again at 12000 G for 15 minutes at 4° C.

The supernatant has been recovered and caused to flow through a chromatography column loaded with 2 mL resin capable of specifically binding the proteins provided with His-tag to Ni$^{2+}$ or, alternatively, to Co$^{2+}$ immobilized on the matrix (Immobilized Metal Affinity Chromatography, IMAC). The latter has been previously equilibrated with the solution F. The chromatography column is washed with the solution A, until the UV/Vis spectrum of the eluate results to be comparable with that of the incoming solution A.

Figure 4:
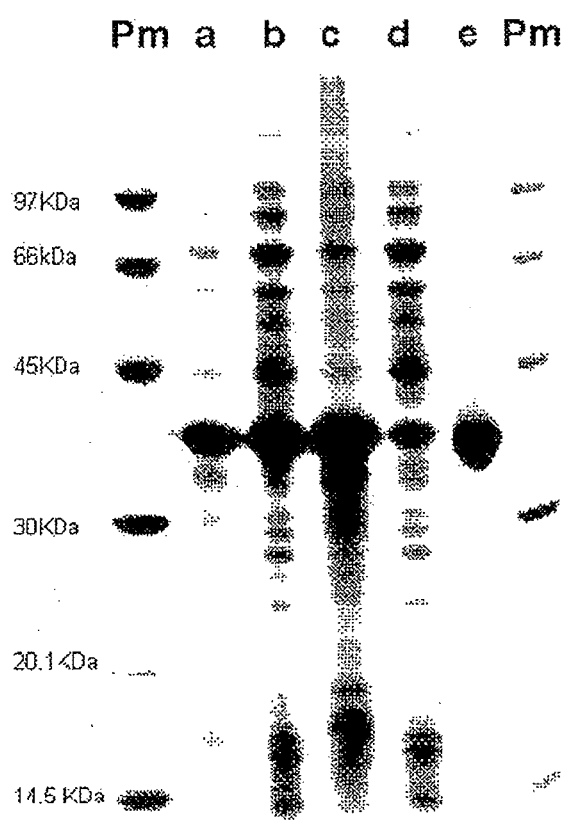
FIG. 4 shows a SDS-page electrophoresis of the samples collected during the purification of the recombinant type V 17β-hydroxysteroid dehydrogenase enzyme, in which: Pm: molecular weight standard; a: cell homogenate; b: supernatant of the centrifuged bacterial lysate; c: pellet of the centrifuged bacterial lysate; d: washing of the chromatography column; e: eluate. The molecular weight expected for the recombinant type V 17β-hydroxysteroid dehydrogenase is 39.2 KDa.

The solution A is thus replaced with the solution G (20 mM Na Phosphate buffer pH 7.4, 500 mM NaCl, 500 mM Imidazole) and the chromatographic profile followed by UV absorption at 280 nm. The moieties corresponding to the absorption peak have been collected and gathered and have been stored in 20% glycerol at −20° C. The protein concentration is evaluated using the Bradford method described below. For every passage an aliquot is hold to monitor the enzyme purity level by means of SDS-PAGE analysis (FIG. 4) carried out according to LammLi method (LammLi U.K.; Cleavage of structural protein during the assembly of the head of bacteriophage T4. Nature 227, 680-685 (1970)).

The loaded amounts of each sample have been calculated based on the respective dilution factor. The mass calculated for the protein in native form is 37 KDa; for the recombinant form, added with his-tag and thrombin cleavage site, is 39.2 KDa. The SDS-PAGE analysis has confirmed the high enzyme expression level and a good purity degree obtained from purification, which is sufficient for industrial application (see FIG. 4/e).

Middle Scale Expression and Purification of the Recombinant Murine Type V 17β-Hydroxysteroid Dehydrogenase Enzyme Under sterile conditions in a 10 mL inoculum tube at 0° C., 200 μl of chemically competent BL21 cells ($CaCl_2$) and 1 μg of the plasmid obtained according to what has been described in the above paragraph have been loaded. This has been left to incubate at 0° C. for 40-60 minutes, then has been transferred to a thermostated bath at 42° C. for 90 seconds. Then it was cooled down to 0° C. for 1-2 minutes and then 1 mL of a standard culture medium (SOC) was added and it was left to incubate at 37° C. for 1 h. The suspension was then transferred into a centrifuge tube and centrifuged at 6000 G for 5 minutes at room temperature. 800 μl of supernatant was removed by siphoning and the pellet was resuspended in the remaining 400 μl. Two plates of LB agar containing 50 μg/mL kanamycin (SOLUTION A) were prepared and pre-heated at 37° C.

The first plate was loaded with 360 μl of the cell suspension and the second plate (diluted) with the remaining 40 μl of the cell suspension. The plates were incubated at 37° C. overnight (about 14 hours) under stirring at 190 rpm.

In a 2 L sterile flask 300 mL of liquid LB containing 50 μg/mL kanamycin (SOLUTION B) was loaded. With a sterile loop several colonies were collected from the plate with individual colonies and were transferred in a flask (about 1 to 5 dead space): CULTURE 1. This was left to incubate at 37° C. overnight (about 14 h) at 190 rpm.

3 6 L flasks were prepared and 2 L SOLUTION B was loaded into each one of them. 100 mL of CULTURE 1 was inoculated in each of them and this was left to incubate at 37° C. and 190 rpm.

By means of IPC, the optical density (OD) value was measured every 10 minutes at 600 nm (up to an absorbance value of about 1 the LB solution not inoculated being the blank).

0.4 mL SOLUTION C was loaded into each flask in order to induce protein expression thereby obtaining a final concentration of IPTG (isopropyl-b-D-thiogalactopyranoside) in the 0.1 mM flask. This was left to incubate for 18 hours at 37° C. and 200 rpm. After 18 hours this was left to cool at 4° C., which temperature was maintained for the remaining procedure.

The optical density (OD) value was measured and 1/OD mL milliliter suspension amount was taken. This aliquot was centrifuged in 1.5 mL Eppendorf, the supernatant was eliminated and the pellet was resuspended in 100 μl SB-1X (SOLUTION D). This sample was then loaded in the final gel. The culture broth obtained was collected and centrifuged at 6000 G for 10 minutes at 4° C. The supernatant was eliminated, the total bacterial pellet was gathered and resuspended in 800 mL phosphate buffer 100 mM at pH 7.4. This was again centrifuged at 6000 G for 10 minutes at 4° C.

The supernatant was eliminated and the residue was resuspended in 100 mL phosphate buffer 100 mM at pH 7.4. The lysis of the cells was then carried out by means of sonication with 10 sonications lasting 15 seconds at 1 minute intervals at 0° C. This was centrifuged again at 12000 G for 10 minutes at 4° C. The supernatant was recovered.

100 μl supernatant was taken and diluted with 50 μl SB3X (SOLUTION E). This sample was loaded in the final gel.

The pellet was resuspended (which would be then eliminated) in 100 mL SOLUTION F. 100 μl suspension was taken up and diluted with 50 μl SB3X (SOLUTION E). This sample would be loaded in the final gel.

The supernatant could be stored at 4° C. and had to be purified as soon as possible.

In order to carry out the purification, a chromatography column was loaded with 50 mL $Ni^{2+}$ resin for proteins provided with His-tag. The column was equilibrated by causing 500 mL solution 20 mM phosphate buffer pH 7.4, 500 mM NaCl and 5 mM imidazole (SOLUTION F) to flow and it was hold at 1 mL/min flow until at the UV/Vis the spectrum of the incoming SOLUTION F resulted to be equal to that of SOLUTION F exiting from the column at 280 nm. When the equilibration was completed this was loaded and the previously recovered solution of supernatant was eluted at 1 mL/min flow. The elute should be without the wanted enzyme.

Accordingly, 100 μl sample was taken and diluted with 50 μl SB3X (SOLUTION E). This sample would be loaded in the final gel. The column was washed with the bound enzyme by flowing 500 mL buffer SOLUTION (SOLUTION F).

The column was washed until when the incoming UV/Vis spectrum (SOLUTION F) was equal to the SOLUTION F spectrum outgoing from the column at 280 nm.

The protein was thus eluted with 100 mL SOLUTION 20 mM Na phosphate buffer at pH 7.4, 500 nM NaCl and 500 mM imidazole (SOLUTION G).

2 mL aliquots were collected. The elution was considered as finished when the spectrum of the incoming SOLUTION G was equal to the spectrum of the outgoing SOLUTION G at 280 nm.

When the moiety collection was completed, the absorbance of each one was measured at 280 and those with absorbance ≥0.2 were gathered. The SOLUTION G was used as the blank.

The moieties containing the protein were gathered and glycerol was added until a final concentration of 20% V/V was obtained and this was stored at −20° C. Before freezing 100 μl protein solution was taken and diluted with 50 μl SB3X (SOLUTION E). This sample was loaded in the final gel.

100 μl was taken to carry out the activity tests (see the relevant experimental part).

Estimate of the Protein Concentration (Bradford Method)

In a 3 mL cuvette for spectrophotometer 3 mL Bradford reagent plus 100 μl BSA (bovine serum albumin) solution at known concentration (0; 0.25; 0.5; 0.75; 1; 1.25 mg/mL) was added.

In a cuvette, 3 mL Bradford reactive and 100 μl of a 1:50 dilution of the unknown protein solution were added. This was stirred and left to rest for 10 minutes.

The reading at 595 nm of the cuvette with known protein content was then started. Finally, the reading of the cuvette with the unknown solution was carried out.

A concentration vs 595 nm absorbance plot was drawn using the values with known concentration and the points obtained have been interpolated on a straight line. The concentration of the unknown solution has been determined therefrom by means of the previously obtained absorbance value.

The obtained value must be multiplied by 50 (dilution factor).

Activity Test of the Recombinant Murine Type V 17β-Hydroxysteroid Dehydrogenase Enzyme To estimate the specific enzymatic activity of the purified protein, a kinetic study was carried out by means of a spectrophotometer. The conversion of 4-androstene-3,17-dione into testosterone by means of the recombinant murine type V 17β-hydroxysteroid dehydrogenase enzyme involved the equimolar consumption of the NADPH cofactor, which acted as the reducing agent.

The NADPH, like the NADH, is characterized by 340 nm absorption of 6.2 mM$^{-1}$cm$^{-1}$, whereas the oxidized form thereof does not absorb at the same wavelength. As the transformation of the 4-androstene-3,17-dione into testosterone is equimolar to the oxidation of NADPH, by quantifying the consumption of the latter over time as a function of the enzyme milligrams used, the activity units can be estimated, which are intended as substrate micromoles converted per minute per protein milligram (U/mg).

A fresh saturated NADPH solution in phosphate buffer 100 mM at about pH 7 (SOLUTION Q) and a fresh saturated solution of 4-androstene-3,17-dione in phosphate buffer 100 mM at pH 7 (SOLUTION P) were prepared. In a quartz 100 μl cuvette, 1 cm optical path, 96 μl SOLUTION P, 4 μl phosphate buffer 100 mM at pH 7 were added. The blank was measured at 340 nm. The absorbance values at 340 nm were detected every second. In a quartz 100 μl cuvette 96 μl SOLUTION P, 2 μl SOLUTION Q and finally, 2 μl protein elution quantified by Bradford assay were inserted. The solution was blended thoroughly, then the wavelength reading was started at 340 nm and the values thereof were recorded. In a plot, the absorbance values were inserted, which were obtained as a function of time and the curve was interpolated. The highest derivate value within the early seconds of measurement was thus defined.

Figure 5:
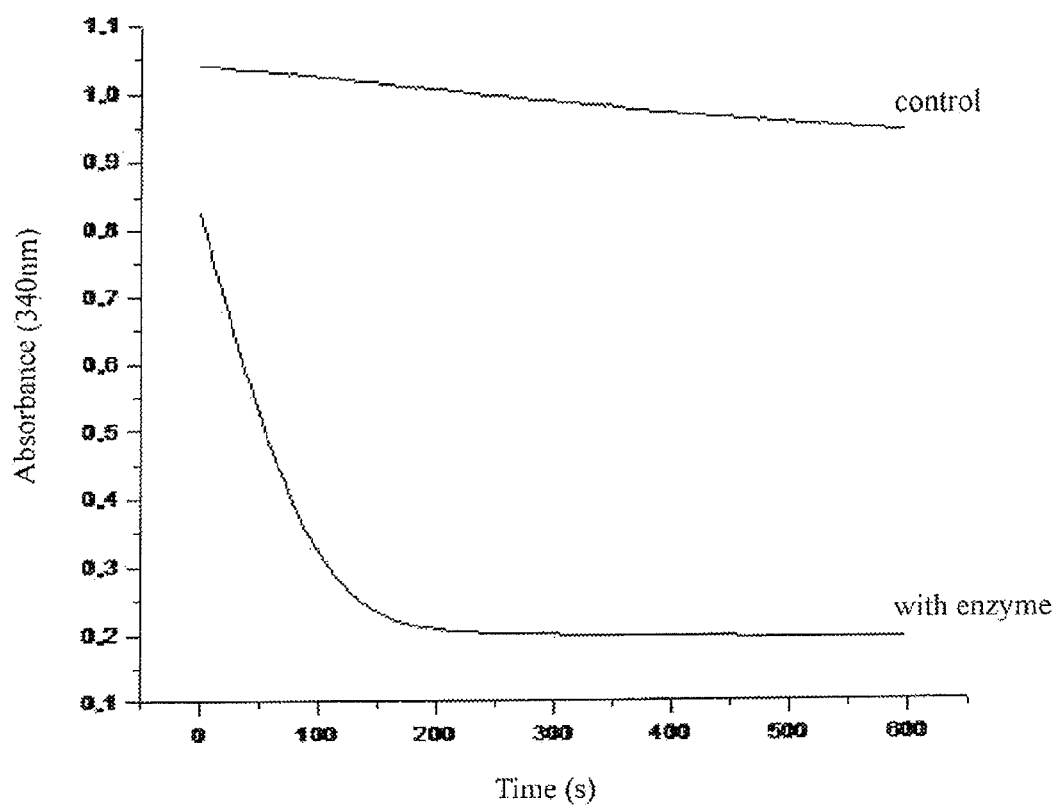
FIG. 5 reports the absorbance plot at 340 nm vs time of a reaction mixture as described herein; it may be appreciated that NADPH is very quickly reduced when an enzyme is present as compared with self-oxidation.

With the values obtained, the plot illustrated in FIG. 5 was drawn, which allows to quantify the NADPH consumption rate at time zero (except the self-oxidation given by the control, consisting of the mixture without enzyme, which must be subtracted) and from the latter the enzyme activity units per protein milligram (U/mg). To calculate the units, the following Formula was used:

Unit/mg=|derivate (s$^{-1}$)|*60 (sec/min)*1 (cm)/
6220 (M$^{-1}$Cm$^{-1}$)*1000000 (M/M)*0.00011/
[(mg/mL sol enzyme*0.002 (mL))]=
(μmol/min)/mg In two different preparations, the values of 0.006 and 0.007 U/mg were obtained.

The present invention is described herein below by means of several illustrating examples which should not be considered as limiting the invention in any way.

The term "inventive enzyme" or "enzyme of the invention" relates to the 17β-recombinant murine type V hydroxysteroid dehydrogenase enzyme described above, which is characterized by the amino acid sequence of SEQ. ID n. 2.

In particular, the enzyme of the invention is the purified 17β-recombinant murine type V hydroxysteroid dehydrogenase of amino acid sequence of SEQ. ID n. 2.

Example 1

The following solutions were prepared:
Solution H (Saturated Solution of 4-Androstene-3,17-Dione)
5 mg of 4-androstene-3,17-dione in
5 mL of buffer solution (phosphate buffer 50 mM; pH 6.5).
This was stirred at 40° C. for 15 minutes and the suspended matter was filtered thereby obtaining a saturated solution of 4-androstene-3,17-dione (conc. 50 μg/mL).
Solution I (NAD Solution)
10 mg of NAD in
1 mL of buffer solution. A clear solution was obtained.
Solution L (NAD Solution)
13 mg of GDH-103 (glucose dehydrogenase) in
1 mL of buffer solution. A clear solution was obtained.

In a thermostated vial provided with magnetic stirring the following was loaded
5 mL of buffer solution,
100 mg of glucose (Fluka),
100 μl of SOLUTION I (equal to 1 mg NAD),
250 μl of SOLUTION L (equal to 1 mg GDH, 60 U),
This was stirred at 30° C. for about 30 minutes, then the following was added
1 mL SOLUTION H (equal to about 50 μg)
40 μl inventive enzyme (equal to about 0.01 U)
This was stirred at 30° C. for about 30 minutes.
The following was carried out:
IPC: HPLC; check of conversion.
After 30 minutes the conversion resulted completed: 100% Testosterone (HPLC A %).
The following was added
1 mL of SOLUTION H (equal to about 50 μg)
This was stirred at 30° C. for about 30 minutes and analyzed by HPLC.
The conversion resulted to be completed (100% Testosterone).

Example 2

A similar test to Example 1 was carried out by loading
50 mg sodium formate instead of glucose,
100 μl of a NADP buffered solution (10 mg NADP dissolved in 1 mL) and
250 μl formate dehydrogenase instead of glucose dehydrogenase (about 14 U),
provided a similar result (complete conversion (100% Testosterone (HPLC A %)) after 30 minutes).

In a thermostated vial provided with magnetic stirring the following was loaded
5.4 mL of buffer solution (phosphate buffer 50 mM; pH 6.5),
0.6 mL of isopropanol
50 mg of sodium formate,
100 μl of NADP solution (obtained by dissolving 10 mg in 1 mL buffer),
250 μl of formate dehydrogenase enzyme (1 mg enzyme equal to about 68 U).
This was stirred at 30° C. for about 30 minutes, then the following was loaded
5 mg of 4-androstene-3,17-dione and
80 μl of the inventive enzyme (equal to about 0.02 U)
This was vigorously stirred at 30° C. for about 2 hours thereby obtaining 99.7% conversion (HPLC analysis).

Example 4

In a thermostated vial provided with magnetic stirring the following was loaded:
6.5 mL of phosphate buffer solution 50 mM a pH 6.5;
0.5 mL of methanol;
0.6 g of glucose (Fluka);
300 μl of 1% NADP solution (cofactor) equal to 3 mg NADP
100 μl of 1% enzyme glucose dehydrogenase solution (1 mg enzyme equal to about 68 U)
This was stirred at 25° C. for about 30 minutes, then the following was loaded
70 mg 4-androstene-3,17-dione and
300 μl Inventive enzyme (equal to about 0.15 U)
This was vigorously stirred at 25° C. for about 40 hours.
The reaction was monitored by HPLC and once completed (98% conversion) 10 mL methylene chloride was added. The phases were filtered to break the emulsion, then the phases were separated and the organic phase was concentrated to residue thereby obtaining Testosterone with a 98% molar yield of isolated product and 98.5% HPLC purity (A %) (contained only 1.5% (A %) 4-androstene-3,17-dione residue).

Example 5

The process described in the Example 4 was repeated by following the same procedure and with the same inventive enzyme, but the NADPH/NADH cofactor, co-solvent type and concentration and the temperature and reaction-time parameters were changed, as illustrated in the following Table 1:

TABLE 1

| NADH/NADPH | co-solvent | % co-solvent | temp. °C. | Time (hours) | conversion |
|---|---|---|---|---|---|
| NADHP | DMSO | 14% | 30 | 90 | 83% |
| NADHP | DMSO | 28 | 30 | 90 | 72% |
| NADHP | DMSO | 43 | 30 | 90 | 48% |
| NADHP | DMSO | 7 | 30 | 44 | 80% |
| NADHP | Acetonitrile | 7 | 30 | 44 | 95% |
| NADHP | DMF | 7 | 30 | 44 | 52% |
| NADHP | DMSO | 7 | 25 | 41 | 90% |
| NADHP | Methanol | 7 | 25 | 41 | 98% |
| NADHP | Ethanol | 7 | 25 | 41 | 97% |
| NADHP | isopropanol | 7 | 25 | 41 | 97% |
| NADHP | tert-butanol | 7 | 25 | 41 | 92% |
| NADHP | Glycerol | 7 | 25 | 140 | 41% |
| NADHP | Pure buffer test | | 25 | 90 | 49% |
| NADH | Methanol | 7 | 25 | 70 | 88% |
| NADH | Ethanol | 7 | 25 | 70 | 61% |
| NADH | Isopropanol | 7 | 25 | 70 | 98% |
| NADH | tert-butanol | 7 | 25 | 70 | 98% |
| NADH | glycerol | 7 | 25 | 70 | 89% |
| NADH | Pure buffer test | | 25 | 70 | 85% |

Example 6

Comparative Example

The process described in the Example 5 was repeated, but employing the cell paste containing wild type murine enzyme Type V 17β-hydroxysteroid dehydrogenase instead of the enzyme of the invention (purified recombinant murine enzyme Type V 17β-hydroxysteroid dehydrogenase). The results are illustrated in Table 2.

TABLE 2

| NADH/NADPH | co-solvent | % co-solvent | temp. °C. | Time (hours) | conversion |
|---|---|---|---|---|---|
| NADHP | Methanol | 7 | 25 | 41 | 56% |

The conversion does not proceed over 56% and the product contains also a mixture of by-products generated by the reduction of the ketonic function in positions 3-α, 3-β and 17-α.

Example 7

Stability Study

Figure 6:
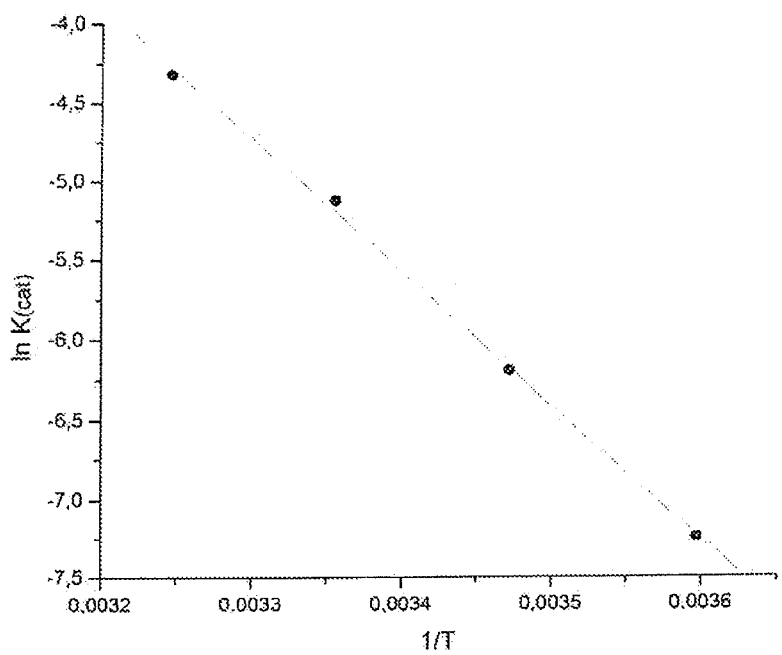
FIG. 6 is an Arrhenius plot, which sets temperature relation against the kinetic constant of the conversion of 4-androstene-3,17-dione to testosterone by the purified recombinant murine type V 17β-hydroxysteroid dehydrogenase enzyme.
Figure 7:
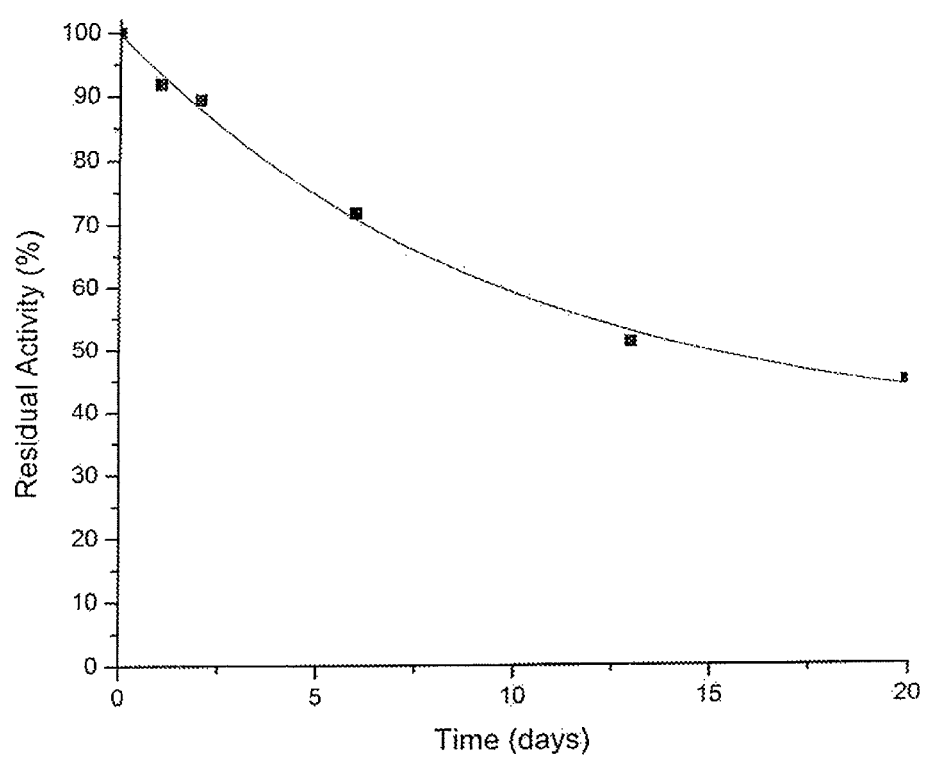
FIG. 7 shows the activity of the enzyme as a function of the time in water at room temperature.

A study to verify the stability in water of the purified recombinant murine enzyme Type V 17β-hydroxysteroid dehydrogenase of the invention was carried out. The FIG. 6 shows the activity of the enzyme as a function of the time in water at room temperature. It can be seen that the enzyme is sufficiently stable to allow industrial biocatalysis as it is still active even after 15 days (Half-life).

Example 8 pH Study

A study to verify the optimal pH for the purified recombinant murine enzyme Type V 17β-hydroxysteroid dehydrogenase of the invention to perform the conversion of androstendione to testosterone was carried out. FIG. 8 shows the activity of the enzyme as a function of the pH in water at room temperature employing two different cofactors. It can be seen that the enzyme shows the highest activity at pH comprised between 5.0 and 7.0. In particular, using NADPH as the co-factor the best pH is 5.5 and using NADH is 6.5-7.0, respectively.

Example 9

Preparation of the Enzyme

A study to optimize the process for the preparation of the purified recombinant murine enzyme Type V 17β-hydroxysteroid dehydrogenase was carried out. The table below shows the activity of the enzyme as a function of the parameters applied for its preparation. It can be seen that the highest activity of the enzyme is reached performing the incubation (protein expression) at a temperature lower than 30° C., particularly preferred is the range between 20° C. and 30° C. The incubation temperature is a key parameter for the preparation of the enzyme.

In view of what has been described above and, in particular the comparison of the results of Example 6—Table 2—and those of Example 5—Table 1 row 8—, those skilled in the art may appreciate the advantages offered by the process of the present invention.

Particularly, it may be appreciated how the recombinant murine type V 17β-hydroxysteroid dehydrogenase enzyme modified as described above enables the purification thereof and makes it is suitable for industrial purposes due to the excellent chemo- and stereoselectivity properties. In addition, the surprisingly high stability allows to obtain optimum results that can be repeated over the time. Furthermore, the enzyme can independently use NADP(H) or NAD(H) as a cofactor, which are both advantageously used in catalytic amounts. The enzyme is capable of catalyzing also the reverse reaction, from testosterone to 4-androstene-3,17-dione, using NAD or NADP as the cofactors.

Advantageously, the enzyme of the present invention is capable of carrying out the catalysis also in water-organic solvent mixtures, such as methanol, ethanol, isopropanol in percentages as high as 50%. This mixtures allow increasing the substrate solubility, which is as low as about 50 μg/mL in water.

In addition, the enzyme has a half-life of more than 15 days in the elution solution (SOLUTION G) at room temperature.

The enzyme activity strongly depends on temperature and solvent type.

The following Table shows the activity of the enzyme as a function of the parameters applied for its preparation.

| Date of preparation | Inoculation vol [ml] | Culture vol (l) | OD induct | Conc. IPTG (mM) | Induct. Temp (° C.) | Induc Time (h) | Final OD | Enzyme Conc. (Bradford) (mg/ml) | Euale Volume (ml) | U/ml | U/mg | Obtained enzyme [mg] | Total Units | mg/l culture | U/l culture |
|---|---|---|---|---|---|---|---|---|---|---|---|---|---|---|---|
| 26/09/08 | 5 | 2.5 | 0.85 | 0.1 | 37 | 18 | 6.32 | 31 | 6.8 | 0.2247 | 0.00725 | 210.8 | 1.5283 | 84.32 | 0.611 |
| 25/03/09 | 200 | 6.2 | 1.6 | 0.1 | 37 | 15 | 6 | 33.22 | 11.5 | 0.4955 | 0.0149 | 162.15 | 5.9682 | 26.15 | 0.919 |
| 22/04/09 | 300 | 6.3 | 1 | 0.1 | 37 | 21 | 6.5 | 25.8 | 27.5 | 0.1470 | 0.0057 | 709.6 | 4.04415 | 112.61 | 0.641 |
| 13/06/09 | 300 | 6.3 | 1 | 0.1 | 39 | 20 | 5.5 | 14.4 | 35 | 0.0566 | 0.00393 | 504 | 1.99072 | 80 | 0.314 |
| 02/07/09 | 700 | 13.9 | 1 | 0.1 | 28 | 24 | 5.9 | 10.5 | 110 | 0.29 | 0.027 | 1155 | 31.9 | 83.09 | 2.294 |
| 09/10/09 | 200 | 19.7 | 1 | 0.1 | 26 | 19 | 10.5 | 48.8 | 76.2 | 0.65 | 0.0133 | 3718 | 49.53 | 188.73 | 2.514 |

As compared with the non purified and unmodified murine type V 17β-hydroxysteroid dehydrogenase enzyme, the enzyme of the present invention has surprisingly shown an excellent chemo- and regioselectivity as well as such a stability as to allow the almost complete, reproducible and exclusive conversion of 4-androstene-3,17-dione to testosterone.

---

The invention claimed is:

1. An industrial process for the synthesis of testosterone comprising the biocatalytic reduction of 4-androstene-3,17-dione using the recombinant murine enzyme Type V 17β-hydroxysteroid dehydrogenase, wherein said recombinant murine enzyme Type V 17β-hydroxysteroid dehydrogenase has the amino acid sequence of SEQ. ID NO: 2.

2. The process according to claim 1, further comprising the use of a cofactor selected from NADP(H) and NAD(H).

3. The process according to claim 2, wherein the cofactor is regenerated in situ.

4. The process according to claim 3, wherein the cofactor is employed in a catalytic amount.

5. The process according to claim 2, further comprising the use of a dehydrogenase enzyme for the regeneration of the cofactor and of a substrate for said dehydrogenase.

6. The process according to claim 5, wherein said dehydrogenase enzyme is selected from the group comprising glucose dehydrogenase and formate dehydrogenase.

7. The process according to claim 5, wherein said enzyme dehydrogenase for the regeneration of the cofactor is glucose dehydrogenase and said substrate is glucose.

8. The process according to claim 5, wherein said enzyme dehydrogenase for the regeneration of the cofactor is formate dehydrogenase and said substrate is sodium formate.

9. The process according to claim 1, wherein said process comprises the use of solvents and/or co-solvents, preferably selected from the group comprising: methanol, ethanol, isopropanol, tert-butanol, glycerol, dimethyl sulfoxide, acetonitrile or dimethylformamide.

10. The process according to claim 1, wherein the pH is kept in the range between 4 and 9 and preferably in the range between 5 and 7.

11. The process according to claim 2, wherein the cofactor is NADPH and the pH is about 5.5.

12. The process according to claim 2, wherein the cofactor is NADH and the pH is about 6.5-7.0.

13. The process according to claim 1, which is carried out at a temperature between 20° C. and 40° C.

* * * * *

SEQUENCE LISTING

<160> NUMBER OF SEQ ID NOS: 4

<210> SEQ ID NO 1
<211> LENGTH: 323
<212> TYPE: PRT
<213> ORGANISM: Mus musculus

<400> SEQUENCE: 1

```
Met Asp Ser Lys Gln Gln Thr Val Arg Leu Ser Asp Gly His Phe Ile
1               5                   10                  15

Pro Ile Leu Gly Phe Gly Thr Tyr Ala Pro Gln Glu Val Pro Lys Ser
            20                  25                  30

Lys Ala Thr Glu Ala Thr Lys Ile Ala Ile Asp Ala Gly Phe Arg His
        35                  40                  45

Ile Asp Ser Ala Ser Met Tyr Gln Asn Glu Lys Glu Val Gly Leu Ala
 50                  55                  60

Ile Arg Ser Lys Ile Ala Asp Gly Thr Val Lys Arg Glu Asp Ile Phe
65                  70                  75                  80

Tyr Thr Ser Lys Val Trp Cys Thr Phe His Arg Pro Glu Leu Val Arg
                85                  90                  95

Val Cys Leu Glu Gln Ser Leu Lys Gln Leu Gln Leu Asp Tyr Val Asp
            100                 105                 110

Leu Tyr Leu Ile His Phe Pro Met Ala Met Lys Pro Gly Glu Asn Tyr
        115                 120                 125

Leu Pro Lys Asp Glu Asn Gly Lys Leu Ile Tyr Asp Ala Val Asp Ile
    130                 135                 140

Cys Asp Thr Trp Glu Ala Met Glu Lys Cys Lys Asp Ala Gly Leu Ala
145                 150                 155                 160

Lys Ser Ile Gly Val Ser Asn Phe Asn Arg Arg Gln Leu Glu Lys Ile
                165                 170                 175

Leu Lys Lys Pro Gly Leu Lys Tyr Lys Pro Val Cys Asn Gln Val Glu
            180                 185                 190

Cys His Pro Tyr Leu Asn Gln Gly Lys Leu Leu Asp Phe Cys Arg Ser
        195                 200                 205

Lys Asp Ile Val Leu Val Ala Tyr Ser Ala Leu Gly Ser His Arg Glu
    210                 215                 220
```

```
Lys Gln Trp Val Asp Gln Ser Ser Pro Val Leu Leu Asp Asn Pro Val
225                 230                 235                 240

Leu Gly Ser Met Ala Lys Lys Tyr Asn Arg Thr Pro Ala Leu Ile Ala
            245                 250                 255

Leu Arg Tyr Gln Leu Gln Arg Gly Val Val Leu Ala Lys Ser Phe
        260                 265                 270

Ser Glu Lys Arg Ile Lys Glu Asn Met Gln Val Phe Glu Phe Gln Leu
        275                 280                 285

Thr Ser Glu Asp Met Lys Val Leu Asp Asp Leu Asn Lys Asn Ile Arg
        290                 295                 300

Tyr Ile Ser Gly Ser Ser Phe Lys Asp His Pro Asp Phe Pro Phe Trp
305                 310                 315                 320

Asp Glu Tyr

<210> SEQ ID NO 2
<211> LENGTH: 343
<212> TYPE: PRT
<213> ORGANISM: Artificial Sequence
<220> FEATURE:
<223> OTHER INFORMATION: modified 17-beta-deidrogenase

<400> SEQUENCE: 2

Met Gly Ser Ser His His His His His His Ser Ser Gly Leu Val Pro
1               5                   10                  15

Arg Gly Ser His Met Asp Ser Lys Gln Gln Thr Val Arg Leu Ser Asp
            20                  25                  30

Gly His Phe Ile Pro Ile Leu Gly Phe Gly Thr Tyr Ala Pro Gln Glu
        35                  40                  45

Val Pro Lys Ser Lys Ala Thr Glu Ala Thr Lys Ile Ala Ile Asp Ala
50                  55                  60

Gly Phe Arg His Ile Asp Ser Ala Ser Met Tyr Gln Asn Glu Lys Glu
65                  70                  75                  80

Val Gly Leu Ala Ile Arg Ser Lys Ile Ala Asp Gly Thr Val Lys Arg
                85                  90                  95

Glu Asp Ile Phe Tyr Thr Ser Lys Val Trp Cys Thr Phe His Arg Pro
            100                 105                 110

Glu Leu Val Arg Val Cys Leu Glu Gln Ser Leu Lys Gln Leu Gln Leu
        115                 120                 125

Asp Tyr Val Asp Leu Tyr Leu Ile His Phe Pro Met Ala Met Lys Pro
    130                 135                 140

Gly Glu Asn Tyr Leu Pro Lys Asp Glu Asn Gly Lys Leu Ile Tyr Asp
145                 150                 155                 160

Ala Val Asp Ile Cys Asp Thr Trp Glu Ala Met Glu Lys Cys Lys Asp
                165                 170                 175

Ala Gly Leu Ala Lys Ser Ile Gly Val Ser Asn Phe Asn Arg Arg Gln
            180                 185                 190

Leu Glu Lys Ile Leu Lys Lys Pro Gly Leu Lys Tyr Lys Pro Val Cys
        195                 200                 205

Asn Gln Val Glu Cys His Pro Tyr Leu Asn Gln Gly Lys Leu Leu Asp
    210                 215                 220

Phe Cys Arg Ser Lys Asp Ile Val Leu Val Ala Tyr Ser Ala Leu Gly
225                 230                 235                 240

Ser His Arg Glu Lys Gln Trp Val Asp Gln Ser Ser Pro Val Leu Leu
                245                 250                 255

Asp Asn Pro Val Leu Gly Ser Met Ala Lys Lys Tyr Asn Arg Thr Pro
            260                 265                 270
```

```
Ala Leu Ile Ala Leu Arg Tyr Gln Leu Gln Arg Gly Val Val Leu
        275                 280                 285

Ala Lys Ser Phe Ser Glu Lys Arg Ile Lys Glu Asn Met Gln Val Phe
        290                 295                 300

Glu Phe Gln Leu Thr Ser Glu Asp Met Lys Val Leu Asp Asp Leu Asn
305                 310                 315                 320

Lys Asn Ile Arg Tyr Ile Ser Gly Ser Ser Phe Lys Asp His Pro Asp
                325                 330                 335

Phe Pro Phe Trp Asp Glu Tyr
            340

<210> SEQ ID NO 3
<211> LENGTH: 23
<212> TYPE: DNA
<213> ORGANISM: Artificial Sequence
<220> FEATURE:
<223> OTHER INFORMATION: forward primer

<400> SEQUENCE: 3
gctgagaaca tatggattct aag                                              23

<210> SEQ ID NO 4
<211> LENGTH: 1269
<212> TYPE: DNA
<213> ORGANISM: Rattus norvegicus

<400> SEQUENCE: 4
gtatcttctc agttggtggg ctgagaagcc atggattcta agcagcagac agtgcgtcta       60
agtgatggtc acttcatccc tatactgggg tttggtacct atgcacctca agaggtacct      120
aagagtaagg ctacagaagc tactaaaata gccatagatg ctggtttccg ccatattgat      180
tcgcttctat gtatcaaaat gaaaaggaag taggactagc catccgaagc aagatagcag      240
atggcactgt gaagagggaa gatatatttt acacatcaaa ggtttggtgt acttttcatc      300
gtccagaact cgtacgggtc tgcttggaac agtcattgaa gcaactccag ttggactatg      360
tggacctgta cctcattcat ttcccaatgg ccatgaagcc gggagaaaat tatctcccaa      420
aagatgaaaa tggaaaatta atatatgatg ctgtggatat ctgtgacacc tgggaagcca      480
tggagaaatg caaggatgca ggattggcca agtccattgg ggtgtccaac tttaaccgca      540
ggcagctgga agatcctg aaaaagccgg ggctcaagta caagcctgtg tgcaaccagg       600
tagaatgtca tccttatctc aatcagggaa aacttctgga tttctgcagg tcaaaagaca      660
ttgttctggt tgcttacagt gctctgggaa gccatcgtga aaaacaatgg gttgatcaga      720
gctctcctgt tcttttggat aatccagttc ttggctcaat ggcaaaaaag tacaatcgaa      780
ctcctgcgct gattgccctt cgctaccagc tacaacgtgg ggttgtggtc ctcgccaaga      840
gtttctctga aagaggata aaagagaata tgcaggtttt tgaatttcag ttgacttcag       900
aggacatgaa agtcctcgat gacctgaata aaaatatccg atacataagt ggttctagct      960
ttaaggacca tcctgatttt ccattttggg atgaatacta actggaggtc catttgtgc     1020 cttgtgccag atgtcactgc attggaagag tgtataggaa gagtattctc aaaatgtgat     1080
gattacatat caccctaatc caagcttctg agcaattctg ctctgctga atctaccatt     1140 ttaaccaaga aagccaaaac tatgtatatt tctcctttct aagaaataaa gaatcgtta      1200 ttctttagca tttaaaaaaa aaaaaaaaag gcggccgct ctagagtatc cctcgagggg     1260
cccaagctt                                                             1269
```